United States Patent
Clarot et al.

(10) Patent No.: US 7,115,275 B2
(45) Date of Patent: Oct. 3, 2006

(54) SYSTEM FOR DELIVERING A COMPOSITION TO THE NASAL MEMBRANE AND METHOD OF USING SAME

(75) Inventors: Tim Clarot, Phoenix, AZ (US); Charles Hensley, Redondo, CA (US)

(73) Assignee: Zicam, LLC, Phoenix, AZ (US)

( * ) Notice: Subject to any disclaimer, the term of this patent is extended or adjusted under 35 U.S.C. 154(b) by 263 days.

(21) Appl. No.: 10/664,839

(22) Filed: Sep. 16, 2003
(Under 37 CFR 1.47)

(65) Prior Publication Data

US 2004/0219107 A1    Nov. 4, 2004

Related U.S. Application Data

(60) Provisional application No. 60/411,463, filed on Sep. 16, 2002.

(51) Int. Cl.
*A61F 13/40* (2006.01)
(52) U.S. Cl. ...................................... 424/434
(58) Field of Classification Search ............... 424/434
See application file for complete search history.

(56) References Cited

U.S. PATENT DOCUMENTS

| | | | |
|---|---|---|---|
| 4,568,326 A | 2/1986 | Rangaswamy | |
| 4,718,889 A | 1/1988 | Blasius, Jr. et al. | |
| 4,826,683 A | 5/1989 | Bates | |
| 4,950,280 A | 8/1990 | Brennan | |
| 4,956,385 A | 9/1990 | Eby, III | |
| RE33,465 E | 11/1990 | Eby, III | |
| 5,100,028 A * | 3/1992 | Seifert | 222/107 |
| 5,248,501 A | 9/1993 | Parnell | |
| 5,288,498 A | 2/1994 | Stanley et al. | |
| 5,578,310 A | 11/1996 | M'Timkulu et al. | |
| 5,622,724 A | 4/1997 | Bryce-Smith | |
| 5,676,643 A | 10/1997 | Cann et al. | |
| 5,708,023 A | 1/1998 | Modak et al. | |
| 5,738,643 A | 4/1998 | Stredic, III | |
| 5,747,058 A | 5/1998 | Tipton et al. | |
| 5,854,269 A * | 12/1998 | Haslwanter et al. | 514/385 |
| 5,895,408 A | 4/1999 | Pagan | |
| 5,908,619 A | 6/1999 | Scholz | |
| 5,954,682 A | 9/1999 | Petrus | |
| 6,139,864 A | 10/2000 | Durr et al. | |
| 6,235,312 B1 | 5/2001 | Hobbs et al. | |
| 6,344,210 B1 | 2/2002 | Fust | |
| 6,350,465 B1 | 2/2002 | Jonnalagadda et al. | |
| 6,365,624 B1 * | 4/2002 | Davidson et al. | 514/494 |
| 6,406,451 B1 | 6/2002 | Rowe | |
| 2001/0007651 A1 | 7/2001 | Fust | |
| 2001/0018077 A1 | 8/2001 | Shaner | |
| 2002/0006961 A1 | 1/2002 | Katz et al. | |
| 2002/0172644 A1 | 11/2002 | Haslwanter et al. | |
| 2002/0193417 A1 | 12/2002 | Seidel et al. | |

FOREIGN PATENT DOCUMENTS

| | | |
|---|---|---|
| DE | 2839793 A1 | 5/1979 |
| EP | 147476 A1 | 7/1985 |
| EP | 0 357 261 A | 3/1990 |
| JP | 61068413 A2 | 4/1986 |
| JP | 05124955 A2 | 5/1993 |

OTHER PUBLICATIONS

ABSTRACT: Abd El-Bary, A. et al.; "Bioavailability of Glibenclamide From Nasal Delivery Systems"; Journal; 1991; Pharmazeutische Industrie; 53(12); pp. 1151-1155.
ABSTRACT: Wasicko M.J. et al.; "The Role of Vascular Tone in the control of Upper Airway Collapsibility"; Journal; American Review of Respiratory Disease; Jun. 1990; 141(6) pp. 1569-1577.
ABSTRACT: Kumar V. et al.; "Aqueous vs Viscous Phenylephrine. I. Systemic Absorption and Cardiovascular Effects"; Journal; Archives of Ophthalmology; Aug. 1986; 104(8); pp. 1189-1191.

* cited by examiner

*Primary Examiner*—Johann R. Richter
*Assistant Examiner*—James Henry Alstrum-Acevedo
(74) *Attorney, Agent, or Firm*—Snell & Wilmer L.L.P.

(57) ABSTRACT

A quick and easy system and method for delivering a composition to a nasal membrane is presented. The applicator assembly includes a sleeve member which encases a swab having a portion that contacts a gelled composition. The sleeve member is manually severed to expose the applicator and the composition. The gelled composition contained on the applicator is applied to the nasal membrane.

33 Claims, 1 Drawing Sheet

SYSTEM FOR DELIVERING A COMPOSITION TO THE NASAL MEMBRANE AND METHOD OF USING SAME

CROSS-REFERENCE TO RELATED APPLICATIONS

This application claims the benefit of provisional application Ser. No. 60/411,463, entitled System and Method for Delivering a Composition to the Nasal Membrane, filed Sep. 16, 2002.

FIELD OF INVENTION

The present invention relates generally to a system and method for delivering a composition to a nasal membrane, and more particularly, to a delivery system which includes an applicator assembly and composition for application of the composition to a nasal membrane.

BACKGROUND OF THE INVENTION

Cold and allergy relief remedies are typically sold in liquid or capsule formulations and are generally administered orally. Although such remedies may work well for relieving some allergy or cold symptoms, the effectiveness of many of these remedies may be limited due to, for example, digestive processes in the oral and digestive pathways. For example, enzymatic activity in the oral cavity and/or acidic environments present in the digestive system may degrade the performance of specific elements or compounds comprising active substances in cold or allergy relief compositions. A further disadvantage of typical compositions involves the circuitous routes some active ingredients are forced to travel, such as when orally administered substances must travel from the oral cavity to the nasal cavity for interaction with active sites in the nasal membrane. For example, these difficulties may be particularly acute when orally administered zinc must travel from the oral cavity up to the ICAM-1 receptor sites on the nasal membrane. Further, effective migration of these active substances may be further impeded when taken by a congested person, often the type of person most in need of these types of nasally bound substances, where the route from the oral cavity to the nasal cavity is blocked or partially blocked by the congestion. Accordingly, a method of delivering active substances to the body which bypasses these degenerative systems is desirable.

Other approaches include administering a medicament directly into the nasal cavity. Many prior attempts at nasal drops and sprays have failed because the active ingredient fails to remain in contact with the nasal membrane for a sufficient period of time, thereby preventing the effective rendering of therapeutically acceptable benefits. For example, typical nasal drops and sprays contain liquid matrices having a low viscosity. Upon application, the liquid tends to be drawn out of the nasal cavity by gravity. The active substance is then prevented from contacting the nasal membrane for an extended period of time sufficient to render a desired therapeutic benefit. For example, some sprays have been observed to dissipate from the nasal cavity in less than five minutes after a first application, which may not allow some active ingredients to remain in contact with the nasal membrane for a sufficient amount of time.

Various methods have been developed attempting to prevent the liquid from dissipating from the nasal cavity, including insertion of nose plugs into the nasal cavity to prevent leakage. Here too, however, prior methods have proved problematic. Consumers tend to find nose plugs of any type uncomfortable and view them as cosmetically unappealing. Such devices also discourage additional applications of the composition to the nasal membrane as the plug must be removed and reinserted each time. Finally, most plugs tend to contact the nasal membrane directly for an extended period of time, which tends to draw the composition away from the nasal membrane due to the absorbent effects of the various materials used to make the plugs.

Accordingly, an improved system for delivering a composition to a nasal membrane is needed which ensures adequate therapeutic results. Moreover, a method is needed for delivering a composition to the nasal membrane that is capable of maintaining contact with the nasal membrane for an effective amount of time to obtain therapeutic results.

SUMMARY OF THE INVENTION

The present invention is generally directed to a method and system for applying a composition to a nasal membrane.

In accordance with one embodiment of the present invention, the system includes an applicator and a composition with a viscosity sufficient to maintain contact with the nasal membrane for a suitable period of time while still allowing efficient migration of a substance across the composition for delivery of the substance to the nasal membrane. In accordance with various aspects of this embodiment, the applicator includes a swab connected to a handle or stick. In accordance with various other aspects of the invention, the composition includes one or more active ingredients such as moisturizers, decongestants, and homeopathic agents. In accordance with yet additional aspects of this embodiment, the system includes a container for enclosing the applicator and the composition.

In accordance with another embodiment of the present invention, the system includes an applicator and a composition with a viscosity greater than about 1500 centipoise. In accordance with various aspects of this embodiment, the applicator includes a swab connected to a handle or stick. In accordance with various other aspects of the invention, the composition includes one or more active ingredients such as moisturizers, decongestants, and homeopathic agents. In accordance with yet additional aspects of this embodiment, the system includes a container for enclosing the applicator and the composition.

In accordance with yet another embodiment of the present invention, the system includes an applicator and a gelled-matrix composition. In accordance with various aspects of this embodiment, the applicator includes a swab connected to a handle or stick. In accordance with various other aspects of the invention, the composition includes one or more active ingredients such as moisturizers, decongestants, and homeopathic agents. In accordance with yet additional aspects of this embodiment, the system includes a container for enclosing the applicator and the composition.

The present invention provides a convenient method and system for applying a composition to a nasal membrane. These and other advantages of the various compositions, methods and systems according to various aspects of the present invention will be apparent to those skilled in the art upon reading and understanding the detailed description below.

BRIEF DESCRIPTION OF THE DRAWINGS

Additional aspects of the present invention should become evident upon reviewing the non-limiting embodiments described in the specification taken in conjunction with the accompanying figures, wherein like numerals designate like elements, and.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present invention.

DETAILED DESCRIPTION

The following descriptions are of exemplary embodiments of the invention only, and are not intended to limit the scope, applicability or configuration of the invention in any way. Rather, the following description is intended to provide a convenient illustration for implementing various embodiments of the invention. As will become apparent, various changes may be made in the arrangement of elements and content of the compositions described herein without departing from the spirit and scope of the invention. For example, though not specifically described, variations in the shape and orientation of the container in the applicator system should be understood to fall within the scope of the present invention. Further, variations in the contents of the composition should also be understood to fall within the scope of the present invention as defined in the claims.

Figure 1:
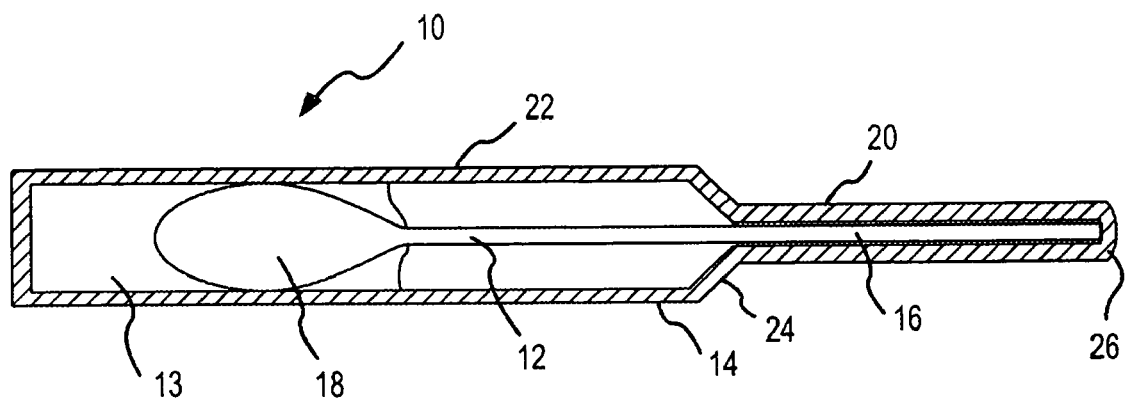
FIG. 1 is a cross-sectional illustration of an applicator system of the present invention.
Figure 2:
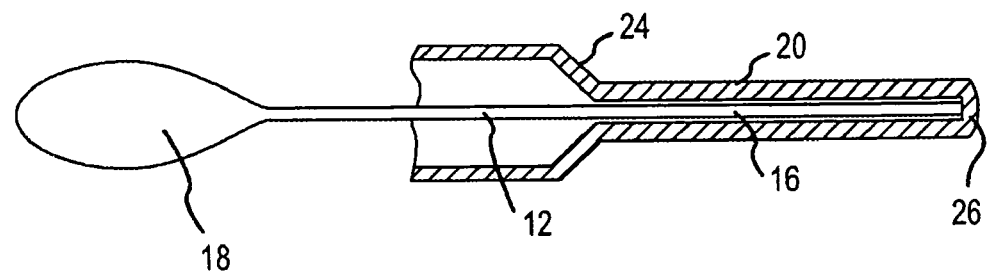
FIG. 2 illustrates a portion of the severed container removed to expose an applicator of the system.

FIGS. 1 and 2 illustrate an exemplary system 10 in accordance with one embodiment of the present invention. System 10 includes an applicator, e.g., a swab 12, a composition 13, and a container 14. As explained in more detail below, system 10 is generally configured to allow quick access to a sealed composition and to facilitate application of composition 13 to a nasal membrane. Generally, systems in accordance with the present invention include an applicator and a composition, which may be sealed to shield the applicator and/or composition from an environment prior to application of the composition.

Applicator 12 is generally configured to assist in removal of composition 13 from container 14 and to aid application of composition 13 to a portion of a nasal membrane. In the illustrated embodiment, applicator or swab 12 includes a straight stick or handle portion 16 and a portion 18 at one end of stick 16. Portion 18 may comprise any suitable material in any suitable shape. For example, portion 18 may include absorbent material such as cotton in a generally bud-type shape, a bud-type shape formed from a sponge or similar material, or other configurations of similar materials.

Container 14 provides a sealed environment for applicator 12 and composition 13. Container 14 is desirably easy to sever such that a user can easily access applicator 12 and composition 13.

Exemplary container 14 is a hollow cylinder which varies in diameter along its length and is preferably comprised of a plastic. Container 14 includes a portion having a small diameter cylinder 20 which can be used as a handle, a portion 22 having a larger cross-section (e.g., diameter) which is used to retain portion 18 of swab 12, and a transition portion 24 between cylinder 20 and portion 22. Container 14 may also include and end 26 that is configured to engage and secure swab 12 in place within container 14. Portion 18 of swab 12 resides in larger portion 22 and contacts a composition in accordance with the present invention which is later described.

As previously stated, it will be understood by those skilled in the art that container 14 may comprise a variety of configurations and shapes. Container 14 may also be comprised of various materials that are capable of being easily and/or manually severed upon application of force. Exemplary materials suitable for container 14 include soft metals, foils, and a variety of plastic materials. It will also be understood by those skilled in the art that portion 22 of sleeve member 14 may be filled with a composition in accordance with the present invention to ensure that an adequate amount of composition is retained on applicator 18 prior to application.

Various exemplary compositions suitable for system 10 will now be described. Although specific compositions are provided below, the invention as set forth herein is not so limited.

In accordance with one embodiment of the invention, composition 13 has a viscosity greater than about 1,500 centipoise. In accordance with various aspects of this embodiment, the viscosity of composition 13 is between about 1,500 to about 40,000 centipoise, preferably about 2,500 to about 10,000 centipoise, and more preferably about 4,000 to about 6,000 centipoise. As described in more detail below, compositions in accordance with this and other embodiments may include one or more materials that alter a the viscosity of the material, one or more active ingredients, and other, additional components.

In accordance with one aspect of this embodiment, the composition has a viscosity in the range of about 1500–2500 centipoise. An exemplary composition in accordance with this aspect has a viscosity in the range of about 1700 to about 2300 centipoise. Another composition in accordance with this aspect has a viscosity in the range of about 1800 to about 2200 centipoise, and yet another composition has a viscosity in the range of about 1900 to about 2100 centipoise. In accordance with still further aspects of this embodiment, the composition has a viscosity in the range of about 1750 to about 2450 centipoise, and in accordance with yet a further aspect, the composition has a viscosity in the range of about 1500 to about 2100 centipoise, and in accordance with yet a further aspect, the composition has a viscosity of about 1800 to about 2500 centipoise.

One exemplary composition in accordance with this aspect of the invention includes an active ingredient. Exemplary active ingredients include homeopathic materials, naturopathic materials, zinc, decongestants, moisturizers, and the like. The composition may also include one or more thickening agents. Suitable thickening agents (e.g., a substance which increases the viscosity of the composition, causes the composition to gel or coagulate, or the like), include materials such as food-grade or pharmaceutical grade thickeners, including, for example, glycerin, carrageenan, sugar, guar gum, methylcellulose, hydroxyethyl cellulose, aloe vera, and the like. The composition may also include other gels, gelling agents, antiseptics, preservatives, permeation enhancers, sequestering agents, buffers, emulsifiers, and any other suitable substance.

Compositions in accordance with another aspect of this embodiment of the invention have a viscosity in the range of about 2500 to about 6000 centipoise. An exemplary composition in accordance with this aspect of this exemplary embodiment has a viscosity in the range of about 5000 to about 6000 centipoise. Another composition in accordance with this aspect has a viscosity in the range of about 4000 to about 6000 centipoise, and yet an additional composition has a viscosity in the range of about 4000 to about 5000 centipoise. In accordance with still further aspects of this embodiment, the composition has a viscosity in the range of about 4500 to about 6000 centipoise, and in accordance with yet a further aspect, the composition has a viscosity in the range of about 2500 to about 4000 centipoise, and in accordance with yet a further aspect, the composition has a viscosity of about 3000 to about 5500 centipoise.

One exemplary composition in accordance with this aspect of the invention includes an active ingredient, such as those described herein The composition may also include one or more thickening agents, as described above. The composition may further include other gels, gelling agents, antiseptics, preservatives, permeation enhancers, sequestering agents, buffers, emulsifiers, and any other suitable substance, as described in more detail below.

Compositions in accordance with yet a further aspect of this embodiment of the invention have a viscosity in the range of about 5000 to about 40,000 centipoise. An exemplary composition in accordance with this aspect of this exemplary embodiment has a viscosity in the range of about 6000 to about 40,000 centipoise. Another composition in accordance with this aspect has a viscosity in the range of about 5000 to about 8000 centipoise, and yet additional compositions has a viscosity in the range of about 5500 to about 10,000 centipoise. In accordance with still further aspects of this embodiment, the composition has a viscosity in the range of about 6000 to about 8000 centipoise, and in accordance with yet a further aspect, the composition has a viscosity in the range of about 6000 to about 10,000 centipoise, and in accordance with yet a further aspect, the composition has a viscosity of about 6000 to about 20,000 centipoise.

Similar to the specific exemplary compositions provided above, one exemplary composition in accordance with this aspect of the invention includes an active ingredient, such as those described herein. The composition may also include one or more thickening agents, as described above, other gels, gelling agents, antiseptics, preservatives, permeation enhancers, sequestering agents, buffers, emulsifiers, and any other suitable substance, as described in more detail below.

Viscosity measurements recited herein were obtained using the Brookfield Syncho-Lectric Viscometer for the measurement of the apparent viscosity of Newtonian and Non-Newtonian materials at low shear rates at given rotation speeds according to ASTM D1824087. See also ASTM D1084–88. As described further herein below, viscosity measurements may be made prior to or after administration of the composition, such as after application from a nasal applicator system as described in accordance with the present invention. In accordance with various embodiments of the invention, the composition may thicken where the composition is admixed with other components.

In accordance with one embodiment of the invention, composition 13 is a gelled-matrix composition. In accordance with various aspects of this embodiment of the invention, the gelled-matrix includes at least one fluid component and one thickener component. Exemplary fluid components include any suitable fluid or liquid, such as, for example, water, oil, alcohol, etc. Likewise, the thickener component may include any acceptable thickener (e.g., a substance which increases the viscosity of the composition, causes the composition to gel or coagulate, or the like), such as food-grade or pharmaceutical grade thickeners, including, for example, glycerin, carrageenan, sugar, guar gum, methylcellulose, hydroxyethyl cellulose, aloe vera, and the like. In various other embodiments, the gel matrix may also include other gels, gelling agents, antiseptics, preservatives, permeation enhancers, sequestering agents, buffers, emulsifiers, and any other suitable substance. Further, as described below, the gel matrix may also include an active substance which is maintained in direct contact with the nasal membrane.

In accordance with various aspects of this embodiment, composition 13 includes from about 75% to about 99.999% or 90 to about 99.1 by weight of at least one carrier, and from about 0.000001% to about 10.0% by weight of an a effective amount of an active substance, and more preferably from about 90% to about 99.999% by weight of at least one carrier, and from about 0.001 to about 5% of an effective amount of an active substance. By way of one particular example, the carrier comprises a mixture of purified water and glycerin, for example, about 90.0% to 99.0% by weight purified (de-ionized) water, and about 0.05 to 5.0% by weight of glycerin.

It should be appreciated that the "gelled matrix compositions" of the present invention may have appreciable viscosity. The previously detailed viscosity limits are not necessarily applicable to or limiting as to the gelled matrix composition or other embodiments of the present invention.

In accordance with yet another embodiment of the invention, composition 13 includes a material configured to remain in contact with a nasal membrane for an extended period of time after the material is applied to the membrane. In accordance with one aspect of this embodiment, composition 13 is also configured to allow diffusion of a substance through a portion of the composition.

In accordance with this embodiment of the invention, after application of composition 13 to the nasal membrane, an interface layer is thought to form between the gelled composition and the nasal membrane. As the active substance is delivered to the nasal membrane, the concentration of active substance at the interface layer becomes depleted. Due to the unique properties of the gel, additional amounts of the active substance are permitted to travel down the resulting concentration gradient, from higher concentration to lower concentration, to replenish the concentration of active substance at the interface layer, thereby further driving additional amounts of active substance into contact with the nasal membrane.

When the composition 13 is so configured, it is believed that the active substance is permitted to diffuse through the composition to the nasal epithelial membrane or mucous of the epithelial membrane. This facilitates the availability of a regular supply of active substance, because diffusion within the composition continues to supply the active substance without requiring that the portion of the composition adjacent to the nasal epithelial membrane (or mucous on the membrane) dissolve or dissipate and expose a fresh portion of the composition containing the active substance.

In accordance with the various embodiments of the present invention, such as those described above, composition 13 may include an active substance or ingredient. As used herein, an active substance includes any of one or more substances that produces or promotes a beneficial therapeutic, physiological, homeopathic and/or phamalogical effect on the body. Such beneficial effects may be brought upon any animal or human patient, and various systems associated therewith, including the immune system, respiratory system, circulatory system, nervous system, digestive system, urinary system, reproductive system, endocrine system, muscular system, skeletal system, and the like, as well as any organs, tissues, membranes, cells, and subcellular components associated therewith.

As will be appreciated by those skilled in the art, beneficial effects include assisting the more efficient functioning of the various systems described above, such as, for example, helping the body fight sickness and disease, helping the body to heal, etc. Exemplary active substances include any element, composition or material producing a beneficial effect, including vitamins, minerals, nucleic acids, amino acids, peptides, polypeptides, proteins, genes, mutagens, antiviral agents, antibacterial agents, anti-inflammatory agents, decongestants, histamines, anti-histamines, anti-allergens, allergy-relief substances, homeopathic substances, naturopathic substances, pharmaceutical substances, and the like.

In accordance with the various embodiments of the invention, composition 13 includes zinc. Zinc may act as a decongestant and/or provide other therapeutic and/or beneficial therapy. It is believed that zinc enhances discharge of mucous and inhibits the generation of new mucous. When a composition comprising zinc is applied to the nasal cavity, zinc ions diffuse from the composition into the mucous or mucous membrane in the nasal cavity. It is believed that the zinc concentration in the mucous or mucous membrane creates a barrier which inhibits viral infection of the nasal epithelial membrane. In accordance with at least one embodiment, as described above, as ionic zinc is absorbed from the gel into the mucous membrane and other nasal epithelial cells, the composition permits new zinc to diffuse into the nasal membrane. In this case, the composition has micelle cell-like properties which facilitate the diffusion of zinc, and other active substances, through the gel matrix. The homeopathic concentration of zinc ions in the zinc gel of the invention is about 4 millimolar (mM) to about 60 millimolar, preferably about 20 mM to about 44 mM or about 15 mM to about 40 mM. Concentrations of zinc in excess of 44 mM are generally not preferred unless an antioxidant or other component is included in the gel composition to protect the nasal epithelial membrane from abnormally high concentrations of zinc. Compositions in accordance with the present invention may also include about 0.01 to about 5 weight percent, 0.01 to about 0.10, or about 0.9 to about 2.0 weight percent zinc gluconate.

In accordance with various aspects of the invention, the composition used in the applicator system of the present invention may be formulated for reducing congestion. In this aspect, the active substance preferably comprises a decongestant—e.g., substances that promote shrinkage of the mucous membrane which makes the breathing process easier, in addition to facilitating drainage of the sinus cavities, substances that promote drying of nasal mucous, discharge of nasal mucous, and the prevention of formation of new nasal mucous. For example, decongestants may include those selected from a group comprising naphazoline hydrochloride, ephedrine, phenylephrine hydrochloride, oxymetazoline hydrochloride (HCL), xylometaxoline hydrochloride and mixtures thereof. Additionally, many aromatic compounds such as those composed primarily of natural oils or extracts therefrom may be decongestants as well such compounds as camphor, eucalyptus oil, menthol, azulen and mixtures thereof. In accordance with exemplary compositions, the decongestant(s) is in a concentration from about 0.000001% to about 0.10% or about 0.01 to about 0.10 by weight.

In accordance with one exemplary embodiment, the decongestant comprises at least oxymetazoline hydrochloride (HCL). Preferably this active substance is present at concentrations from about 0.045% to about 0.055% by weight, and more preferably at about 0.05% by weight.

In accordance with the embodiments of the invention described herein, composition 13 may include glycerin. Glycerin has many properties that facilitate nasal delivery of drugs and other active substances. For example, glycerin supports certain active substances in an ionic state, and permits rapid diffusion of various active substances across the gel matrix. Glycerin also has an ability to permeate nasal mucous and the nasal epithelial membrane, while carrying with it the active substance for appropriate delivery.

Composition 13 may also include thickeners, permeation enhancers, antiseptics, preservatives, buffers, emulsifiers, and any other suitable substance other than the active substance. Composition 13 may also include moisturizers such as aloe vera, glycerin, and the like.

The thickener component or components may be utilized to form colloidal solutions (i.e., suspensions) in order to increase the viscosity of the carrier in the nasal gel composition. Suitable thickeners may include any acceptable thickener, such as food-grade or pharmaceutical-grade thickeners, including, for example, glycerin, carrageenan, sugar, guar gum, methylcellulose, hydroxyethyl cellulose, carbohydrate thickness, aloe barbadensis gel (Aloe Vera), and the like, as well as other gels, gelling agents, antiseptics, preservatives, permeation enhancers, sequestering agents, buffers, emulsifiers, and the like. An exemplary concentration for the thickener is about 0.000001% to about 5.0% by weight, preferably about 0.01 to about 3% by weight, and more preferably about 0.5 to about 25 by weight of the composition.

In accordance with exemplary embodiments of the invention, the composition includes from about 0.05% to about 2.5% of by weight of hydroxy cellulose, and preferably about 1.25% by weight of hydroxyl cellulose. In accordance with further embodiments, the thickener also compromises from about 0.00001% to about 1.0% by weight of aloe barbadensis gel (200:1 concentrate), and preferably about 0.001% by weight. Addition of aloe barbadensis gel may be preferred where practitioners seek to utilize its soothing properties in a composition. Alternatively, however, aloe may be provided in a suitable delivery formulation that does not significantly increase viscosity, such as, for example in suitable granulated and/or powdered forms.

The composition may also include permeation enhancers, which are believed to function by enlarging or loosening tight junctions between cells in the nasal membrane, thereby facilitating passage of the active substance therethrough. Permeation enhancers include liposomes, sequestering agents, ascorbic acid (Vitamin C), glycerol, chitosan, and lysophosphotidylcholin, or any other substance that provides a similar function or result. By way of example, the permeation enhancer may include a sequestering agent, such as EDTA. EDTA is thought to chelate calcium. When applied to the nasal membrane, it is believed to remove calcium from the cell junctions, thereby loosening the junctions to facilitate passage of an active substance therethrough.

Permeation enhancers may be present in any effective amount, with preferable concentrations ranging from about 0.00001% to about 5.0% by weight. In an exemplary composition, the permeation enhancer includes disodium EDTA, at a concentration of about 0.0001% to about 1.0% by weight, and preferably at about 0.10% by weight.

In accordance with another aspect of the invention, a preservative may be added to the composition to facilitate stability of the various ingredients. Any suitable preservative may be used in accordance with the present invention.

Exemplary preservatives include a 50% solution of benzalkonium chloride, admixed into the composition at a concentration of about 0% to about 0.1% by weight, about 0.001 to 0.06% by weight, or 0.03% to about 0.06% by weight. Benzalkonium chloride may be preferred due to its recognized properties as an antiseptic. In a further embodiment, the preservative also comprises an alcohol such as benzyl alcohol, at a concentration of about 0 to about 2% by weight, about 0.0001% to about 1.0% by weight, or about 0.1 to about 0.3% by weight. The preservative may also comprise from about 0.001% to about 1.0% by weight or about 0.10% by weight disodium EDTA. It is believed disodium EDTA facilitates stability by combining with metals (chelating) and further by preventing various oxidative processes, as well understood by skilled practitioners in the art.

An emulsion agent, or emulsifier, may also be added to the composition in accordance with the present invention. The emulsifier may be selected from a group containing hydrophobic and hydrophilic substituents, such as glycerolpolyethylene glycol ricinoleate, fatty acid esters of polyethyleneglycol, ethoxylated glycerol, polyethylene glycol, and mixtures thereof. By way of particular example, the composition may emulsifier include an emulsion agent such as hydroxylated lecithin, present at a concentration from about 0 to 2% by weight, about 0.00001% to about 1.0% by weight, or about 0.001% to about 0.002 by weight.

The composition may also include at least one buffer. Any suitable buffer may be used in accordance with the present invention. In an exemplary embodiment, the composition includes from about 0 to about 4 weight percent buffer such as disodium phosphate (heptahydrate), about 0.0001% to about 3.0% by weight disodium phosphate, or about 1 to 2% by weight of disodium phosphate, and from about 0 to about 4%, 0.0001% to about 3.0%, or 1 to 2 percent by weight of monosodium phosphate (monohydrate).

EXAMPLES

The Examples set forth hereinbelow are illustrative of various aspects of certain exemplary embodiments of the composition used in the applicator system of the present invention. The compositions, methods and various parameters reflected therein are intended only to exemplify various aspects and embodiments of the invention, and are not intended to limit the scope of the claimed invention.

Example 1

An exemplary gel composition for relieving congestion used in the applicator delivery system of the present invention is prepared by admixing the following ingredients as follows:

| Component | Amount % w/w |
|---|---|
| Oxymetazoline HCL | 0.05% |
| Alkoxylated Diester | 0.001% |
| Aloe Barbadensis Gel (200:1 Concentrate) | 0.001% |
| Benzalkonium Chloride (50% solution) | 0.04% |
| Benzyl Alcohol | 0.20% |
| Disodium EDTA | 0.10% |
| Disodium Phosphate (Heptahydrate) | 1.12% |
| Glycerin | 1.00% |
| Hydroxyethylcellulose | 1.25% |
| Hydroxylated Lecithin | 0.001% |
| Monosodium Phosphate (Monohydrate) | 2.31% |
| Purified Water | 93.927% |

The viscosity of the composition is believed to initially fluctuate over time, but soon substances stabilize at three (3) months after initial formation of the gel composition. For example, viscosity of the above formulation may be as follows:

t (0)-7,000 to 8,000 centipoise
t (1 month)-4,000 to 5,000 centipoise
t (2 months)-5,000 to 6,000 centipoise
t (3 months)-4,500 to 5, 000 centipoise;

where t equals time in months from initial composition preparation. Viscosity is generally scheduled at 3 months and greater.

Example 2

An exemplary gel composition for relieving sinus discomfort used in the applicator delivery system is prepared by admixing the following ingredients:

| Component | Amount % w/w |
|---|---|
| Oxymetazoline HCL | 0.05% |
| Alkoxylated Diester | 0.001% |
| Aloe Barbadensis Gel (200:1 Concentrate) | 0.001% |
| Benzalkonium Chloride (50% solution) | 0.04% |
| Benzyl Alcohol | 0.20% |
| Disodium EDTA | 0.10% |
| Disodium Phosphate (Heptahydrate) | 1.12% |
| dl-alpha Tocopherol | 0.01% |
| Eucalyptol | 0.15% |
| Glycerin | 1.00% |
| Hydroxyethylcellulose | 1.25% |
| Hydroxylated Lecithin | 0.001% |
| Menthol | 0.08% |
| Monosodium Phosphate (Monohydrate) | 2.31% |
| Purified Water | 93.927% |

Example 3

An exemplary gel composition used in the applicator delivery system for delivering an effective homeopathic amount of zinc is prepared by admixing the following ingredients:

| Component | Amount % w/w |
|---|---|
| Purified water | 95.8% |
| Glycerin U.S.P | 2.0% |
| Carbopol 940 nf | 0.5% |
| Zinc (Ionic) | 0.21% (33.3 mM) |
| Zinc Gluconate (source of ionic zinc) | 1.50 (33.3 mM) |

Example 4

Another exemplary gel composition used in the applicator delivery system for delivering an effective homeopathic amount of zinc is prepared by admixing the following ingredients:

| Component | Amount % w/w |
|---|---|
| Purified water | ~97.08% |
| Glycerin U.S.P | 1.0% v/v |
| Sodium Chloride | 0.9% |
| Hydroxyethyl Cellulose | 1.2 |
| Zinc Gluconate (14% Zn) (source of ionic zinc) | 1.58 (2 mg.ml) |
| Benzalkonium Chloride (50%) | 0.02% |
| Sodium Hydroxide (20%) | 0.4% |

Example 5

Another exemplary gel composition used in the applicator delivery system for delivering a moisturizing composition is prepared by admixing the following ingredients:

| Components | Weight Percent Range | Exemplary Value |
|---|---|---|
| Purified Water | 95–100.00 | 95.522% |
| Sodium Phosphate | 1.500–3.000 | 1.5% |
| Hydroxyethylcellulose | 1.000–1.500 | 1.0% |
| Disodium Phosphate | 1.000–1.500 | 1.0% |
| Glycerin | 0.750–1.250 | 0.75% |
| Alkoylated Diester | 0.001–0.500 | 0.001% |
| Aloe Barbadensis Gel | 0.001–0.250 | 0.001% |
| Hydrolyzed Algin | 0.001–0.060 | 0.001% |
| Chlorella Vulgaris Extract | 0.001–0.060 | 0.001% |
| Sea Water | 0.001–1.000 | 0.001% |
| Benzalkonium Chloride | 0.010–0.100 | 0.01% |
| Benzyl Alcohol | 0.200–0.500 | 0.20% |
| Disodium EDTA | 0.010–0.100 | 0.01% |
| Hydroxylated Lecithin | 0.001–1.000 | 0.001% |
| Tocopherol | 0.001–0.100 | 0.001% |
| Polysorbate 80 | 0.001–0.100 | 0.001% |

In accordance with yet another embodiment of the invention, composition 13 is delivered into a user's nose using system 10 of the present invention. In accordance with one aspect of this invention, a user is instructed to blow his nose prior to administration of the delivery composition. The user is thereafter instructed to hold the sleeve member 14 with one hand, and apply force to transition portion 24 of sleeve member 14, or twist small diameter cylinder 20 of sleeve member 14 with the other hand to sever sleeve member 14 at the location of transition portion 24. Once sleeve member 14 is severed, the user removes larger diameter cylinder 22 to expose applicator 18 of swab 12 which contains composition 13.

Next, the user is instructed to place portion 18 into the nasal cavity and to gently apply composition 13 to the nasal membrane. The user is instructed to deliver the composition into each nostril.

After application, the user is instructed to depress the outside of each nostril for about 5 seconds. The user is thereafter instructed to reapply the composition to each nostril every 2–4 hours until symptoms subside, and to continue such use for 48 hours.

A application dosage may vary in accordance with factors such as the active ingredient, desired frequency of application, and the like. By way of particular example, when the active ingredient is zinc, an application dosage may be from about 20 to about 100 mg of zinc, about 30 to about 70 mg of zinc, about 30 to about 50 mg of zinc, or about 50 to about 80 mg of zinc.

Applicator system 10 may be produced by inserting swab 12 containing a composition in accordance with the present invention into container 14 so that stick 16 of swab 12 frictionally engages with tip element 26 so that swab 12 is secured in place within sleeve member 14. Upon securing swab 12 in place, applicator 18 will reside within larger diameter cylinder 22 of container 14. Container 14 is then sealed, such as by heat seal, on its open end to create an enclosed, individually packaged applicator system.

An improved system for effectively delivering a composition to the nasal membrane has been presented. The delivery system includes an applicator system having a container or sleeve member which encases an applicator and a composition. In accordance with various embodiments, the composition includes an active substance such as a decongestant, zinc, or the like. Other ingredients may also be added to enhance delivery of the active substances, such as permeation enhancers, certain thickeners, cilia activators, moisturizers, and the like.

The present invention has been described above with reference to a number of exemplary embodiments and examples. It should be appreciated that the particular embodiments shown and described herein are illustrative of the invention and its best mode and are not intended to limit in any way the scope of the invention as set forth in the claims. Those skilled in the art having read this disclosure will recognize that changes and modifications may be made to the exemplary embodiments without departing from the scope of the present invention. For example, the container or sleeve member, as well as the swab, may comprise various shapes, orientations and materials and still fall within the scope of the present invention. In addition, artisans will recognize that the nasal membrane includes any interior surface of the nasal cavity permitting delivery of an active substance to the body, including the epithelial layer of nasal membrane or mucous of the epithelial layer of the membrane. Further, though reference is made both to "substances" and "ingredients," skilled artisans will further appreciate that the two terms can be used interchangeably. Additionally, though various components of the composition are described herein in terms of exemplary embodiments, such as, for example, thickeners, permeations enhancers, emulsifiers, buffers, and preservatives, any suitable composition may include additives now known or hereafter devised. Accordingly, these and other changes or modifications are intended to be included to be within the scope of the present invention, as expressed in the following claims.

We claim:

1. A system for delivering a composition to a nasal membrane comprising:
   an applicator assembly having an elongated stick and an applicator at one end of the stick contained within an elongated container having an enclosed first portion for holding the stick, and an enclosed second portion for encasing the applicator, wherein the elongated container can be severed to create adjacent open ends of the first and second portions thereby freeing the applicator; and
   a composition having a viscosity greater than about 1,500 centipoise enclosed adjacent the applicator.

2. The system of claim 1, wherein the composition comprises an active substance comprising at least one of zinc, a vitamin, a nucleic acid, an amino acid, a peptide, a polypeptide, a protein, a gene, a mutagen, an antiviral agent, an antibacterial agent, an anti-inflammatory agent, a decongestant, a histamine, an anti-histamine, and a moisturizer.

3. The system of claim 2, wherein the active substance is a decongestant comprising at least one of the following: zinc, oxymetazoline hydrochloride, naphazoline hydrochloride, ephedrine, phenylepbrine hydrochloride, xylontetaxoline hydrochloride, camphor, eucalyptus oil, menthol, and azulen.

4. The system of claim 2, wherein the composition having an active substrate further comprises at least one of a carrier, a thickener, a permeation enhancer, a preservative, an emulsifier, and a buffer.

5. The system of claim 4 having a carrier comprising glycerin.

6. The system of claim 4 having a thickener comprising at least one of the following: glycerin, carrageenan, sugar, guar gum, methylcellulose, hydroxyethyl cellulose, carbohydrate thickeners, aloe barbadensis gel, antiseptics, preservatives, permeation enhancers, sequestering agents, buffers, and emulsifiers.

7. The system of claim 4 having a permeation enhancer comprising at least one of the following: liposomes, sequestering agents, ascorbic acid, glycerol, chitosan, lysophosphotidyicholin, EDTA, and disodium EDTA.

8. The system of claim 4 having a preservative comprising at least one of a benzalkonium chloride and a benzyl alcohol.

9. The system of claim 4 having an emulsifier comprising at least one of the following: glyccrolpolyethylene glycol ricinoleate, fatty acid esters of polyethyleneglycol, ethoxylated glycerol, polyethylene glycol, and hydroxylated lecithin.

10. The system of claim 4 having an a buffer comprising at least one of a monosodium phosphate and a disodium phosphate.

11. The system of claim 2 wherein the active substance is zinc gluconate in a range of about 0.9 to about 2.0 weight percent.

12. The system of claim 2 wherein the active substance is zinc in a range of about 15 mM to about 40 mM.

13. The system of claim 11 wherein the composition further comprises about 90 to about 99.1 weight percent of a carrier.

14. The system of claim 13 wherein the carrier includes glycerin.

15. The system of claim 11 wherein the zinc composition further comprises a thickener.

16. The system of claim 15 wherein the thickener is selected from the group consisting of: carbohydrate thickeners, carrageenan, sugar, guar gum, hydroxyethyl cellulose, and methylcellulose.

17. The system of claim 3 wherein the zinc composition further comprises about 0.01 to about 0.10 weight percent methanol.

18. The system of claim 11 further comprising a preservative.

19. The system of claim 18 wherein the preservative comprises at least one of the following: benzalkonium chloride and benzyl alcohol.

20. An applicator assembly for delivering a composition having an active substance to a nasal membrane comprising:
   a sleeve having a handle portion at one end, a receptacle portion at the other end and a transition portion between the two ends wherein the transition portion can be manually severed to separate the handle and receptacle portions of the sleeve; and
   a swab having an elongated stick and an applicator element at one end of the stick contained within the sleeve wherein the applicator holds a composition having a viscosity between about 1,500 centipoise and about 40,000 centipoise.

21. The applicator assembly of claim 20, comprising an active substance selected from the group consisting of zinc, a vitamin, a nucleic acid, an amino acid, a peptide, a polypeptide, a protein, a gene, a mutagen, an antiviral agent, an antibacterial agent, an anti-inflammatory agent, a decongestant, a histamine, an ant-histamine, and a moisturizer.

22. The applicator of claim 21, wherein the active substance is a decongestant comprising at least one of the following: zinc, oxymetazoline hydrochloride, naphazoline hydrochloride, ephedrine, phenylepbrine hydrochloride, xylometaxoline hydrochloride, camphor, eucalyptus oil, menthol, and azulen.

23. The applicator assembly of claim 21, wherein the active substance is zinc.

24. The applicator assembly of claim 23 wherein the active substance is zinc gluconate in a range of about 0.9 to about 2.0 weight percent.

25. The applicator assembly of claim 23 wherein the active substance is zinc in a concentration of about 15 mM to about 40 mM.

26. The applicator assembly of claim 23 wherein the composition further comprises at least one of a carrier, a thickener, a permeation enhancer, a preservative, an emulsifier, and a buffer.

27. The applicator assembly of claim 26 having a carrier comprising glycerin.

28. The applicator assembly of claim 26 having a thickener comprising at least one of the following: glycerin, carrageenan, sugar, guar gum, methylcellulose, hydroxyethyl cellulose, carbohydrate thickeners, aloe barbadensis gel, antiseptics, preservatives, permeation enhancers, sequestering agents, buffers, and emulsifiers.

29. The applicator assembly of claim 26 having a permeation enhancer comprising at least one of the following: liposomes, sequestering agents, ascorbic acid, glycerol, chitosan, lysophosphotidylcholin, EDTA, and disodium EDTA.

30. The applicator assembly of claim 26 having a preservative comprising at least one of a benzalkonium chloride and a benzyl alcohol.

31. The applicator assembly of claim 26 having an emulsifier comprising at least one of the following: glycerolpolyethylene glycol ricinoleate, fatty acid esters of polyethyleneglycol, ethoxylated glycerol, polyethylene glycol, and hydroxylated lecithin.

32. The applicator assembly of claim 26 having an a buffer comprising at least one of a monosodium phosphate and a disodium phosphate.

33. A method for delivering a composition to the nasal membrane comprising the steps of:
   providing an applicator having an elongated stick and a portion at one end of the stick contained within an elongated container having an enclosed first portion for holding the stick, and an enclosed second portion for holding the applicator, wherein the second portion holds a composition having a viscosity between about 1,500 to 40,000 centipoise;
   applying force to the elongated container to sever the container and separate the first and second portions;
   removing the second portion of the elongated container to expose the applicator; and
   applying the composition containing applicator to a nasal membrane.

* * * * *